(12) United States Patent
Rozing et al.

(10) Patent No.: US 8,828,922 B2
(45) Date of Patent: Sep. 9, 2014

(54) HSP THERAPY IN CONJUNCTION WITH A LOW ANTIGENICITY DIET

(75) Inventors: Johannes Rozing, Groningen (NL); Dana Elias, Gedera (IL)

(73) Assignee: Andromeda Biotech Ltd., Rehovot (IL)

(*) Notice: Subject to any disclaimer, the term of this patent is extended or adjusted under 35 U.S.C. 154(b) by 0 days.

(21) Appl. No.: 13/397,399

(22) Filed: Feb. 15, 2012

(65) Prior Publication Data

US 2012/0142588 A1    Jun. 7, 2012

Related U.S. Application Data

(60) Continuation of application No. 12/392,862, filed on Feb. 25, 2009, now abandoned, which is a division of application No. 11/495,919, filed on Jul. 27, 2006, now abandoned, which is a continuation of application No. PCT/IL2005/000100, filed on Jan. 27, 2005.

(60) Provisional application No. 60/539,330, filed on Jan. 28, 2004.

(51) Int. Cl.
| | | |
|---|---|---|
| C07K 14/00 | (2006.01) | |
| A61K 38/16 | (2006.01) | |
| A61K 38/01 | (2006.01) | |
| A61K 38/17 | (2006.01) | |

(52) U.S. Cl.
CPC ............. *A61K 38/164* (2013.01); *A61K 38/018* (2013.01); *A61K 38/1709* (2013.01)
USPC .............................................. 514/1; 530/350

(58) Field of Classification Search
USPC .............................................. 514/1; 530/350
See application file for complete search history.

(56) References Cited

U.S. PATENT DOCUMENTS

| | | | |
|---|---|---|---|
| 5,114,844 A | 5/1992 | Cohen et al. ................... 435/7.21 |
| 5,578,303 A | 11/1996 | Cohen et al. ................... 424/93.71 |
| 5,671,848 A | 9/1997 | Cohen et al. ................... 206/569 |
| 5,780,034 A | 7/1998 | Cohen et al. ............... 424/185.1 |
| 5,993,803 A | 11/1999 | Cohen et al. ................ 424/93.71 |
| 6,110,746 A | 8/2000 | Cohen et al. ................... 436/506 |
| 6,180,103 B1 | 1/2001 | Cohen et al. ............... 424/185.1 |
| 6,451,368 B1 | 9/2002 | Elliott et al. ................... 426/580 |
| 6,451,552 B1 | 9/2002 | Van Beresteijn et al. ..... 435/68.1 |
| 6,488,933 B2 | 12/2002 | Cohen |
| 7,585,618 B2 | 9/2009 | Reimer et al. |

FOREIGN PATENT DOCUMENTS

| | | |
|---|---|---|
| EP | 0 417 271 B1 | 3/1991 |
| WO | WO 95/10537 A1 | 4/1995 |
| WO | WO 96/19236 A1 | 6/1996 |
| WO | WO 97/01959 A1 | 1/1997 |
| WO | WO 98/08536 A2 | 3/1998 |
| WO | WO 98/31239 | 7/1998 |
| WO | WO 01/37850 A2 | 5/2001 |

OTHER PUBLICATIONS

International Search Report, PCT/IL2005/00100, mailed Jun. 25, 2008.
Elias et al., "Peptide therapy for diabetes in NOD mice", Lancet, vol. 343, Issue 8899, pp. 704-706 (1994).
Abulafia-Lapid, R., et al., "T Cell Proliferative Responses of Type 1 Diabetes Patients and Healthy Individuals to Human hsp60 and its Peptides", Journal of Autommunity, vol. 12, pp. 121-129, (1999).
Brugman, S., et al., "Neonatal oral administration of DiaPep277, combined with hydrolysed casein diet, protects against Type 1 diabetes in BB-DP rats. An experimental study", Diabetologia, vol. 47, pp. 1331-1333, (2004).
Bukau, B. et al., "Getting Newly Synthesized Proteins into Shape", Cell, vol. 101, pp. 119-122, (2000).
Brudzynski, Katrina, "Insulitis-Caused Redistribution of Heat-Shock Protein HSP60 Inside Beta-Cells Correlates with Induction of HSP60 Autoantibodies", Diabetes, vol. 42, pp. 908-913 (1993).
Cohen, I.R., "Peptide therapy for Type 1 diabetes: the immunological homunculus and the rationale for vaccination", Diabetologia. vol. 45, pp. 1468-1474, (2002).
Elias, D. et al., "Vaccination against autoimmune mouse diabetes with a T-cell epitope of the human 65-kDa heat shock protein", Proc. Natl. Acad. Sci USA, vol. 88, pp. 3088-3091, (1991).
Elliott, R.B., et al., "Dietary protein: a trigger of insulin-dependent diabetes in the BB rat?", Diabetologia, vol. 26, pp. 297-299, (1984).
Funda D. P. et al., "Gluten-free diet prevents diabetes in NOD mice", Diabetes/Metabolism Research and Reviews, vol. 15, 66. 323-327 (1999).
Gale,Edwin A.M., "Oral tolerance and autoimmune diabetes—will hope triumph over experience?", The Lancet, vol. 356, pp. 526-527, (2000).
Holoshitz, J., et al., "Tlymphocytes of Rheumatoid Arthritis Patients Show Augmented Reactivity to a Fraction of Mycobacteria Cross-Reactive with Cartilage", The Lancet, vol. 2, pp. 305-309, (1986).
Li, X-B, et al., "Low incidence of autoimmune Type 1 diabetes in BB rats fed a hydrolysed casein-based diet associated with early inhibition of non-macrophage-dependent hyperexpression of MHC class I molecules on beta cells", Diabetologia, vol. 38, pp. 1138-1147, (1995).
Scott, Fraser, W., "Food-induced Type 1 Diabetes in the BB Rat", Diabetes/Metabolism Reviews, vol. 12, No. 4, 341-359 (1996).
Scott, Fraser W, et al., "Oral Exposure to Diabetes-Promoting Food or Immunomodulators in Neonates Alters Gut Cytokines and Diabetes", Diabetes, vol. 51, pp. 73-78 (2002).
Leslie, R. David G. et al., "Perspectives in Diabetes Early Environmental Events as a Cause of IDDM Evidence and Implications", Diabetes, vol. 43, pp. 843-850, (1994).
Scott, Fraser W, et al., "Potential Mechanisms by Which Certain Foods Promote or Inhibit the Development of Spontaneous Diabetes in BB Rats, Dose Timing, Early Effect on Islet Area, and Switch in Infiltrate From Th1 to Th2 Cells", Diabetes, vol. 46, pp. 589-598, (1997).
Singh-Jasuja, H., et al., "The Role of Heat Shock Proteins and Their Receptors in the Activation of the Immune System", Biol. Chem. vol. 382, pp. 629-636, (2001).

(Continued)

Primary Examiner — Karen Cochrane Carlson

(74) Attorney, Agent, or Firm — Winstron & Strawn LLP

(57) ABSTRACT

The present invention relates to a method for suppression, prevention, delaying the onset or treatment of diabetes, by administering to an individual in need thereof a fragment of Hsp60 or analog thereof in conjunction with a low antigenicity diet. The invention is exemplified using DiaPep277™, an analog of residues 437-460 of human Hsp60 in combination with a hydrolyzed casein diet.

16 Claims, 2 Drawing Sheets

(56) References Cited

OTHER PUBLICATIONS

Virtanen S. M. et al., "Early Introduction of Dairy Products Associated with Increased Risk of IDDM in Finnish Children", Diabetes, vol. 42, pp. 1786-1790, (1993).

Visser, J., et al., "Short-Term Dietary Adjustment With a Hydrolyzed Casein-Based Diet Postpones Diabetes Development in the Diabetes-Prone BB Rat", Metabolism, vol. 52, No. 3, pp. 333-337, (2003).

Yoon, Ji-Won et al., "Cellular and Molecular Pathogenic Mechanisms of Insulin-Dependent Diabetes Melitus", Annals of the NY Academy of Sciences, pp. 200-211 (2001).

Zugel, U. et al., "Immune Response against Heat Shock Proteins in Infectious Diseases", Immunobiology, vol. 201, pp. 22-35, (1999).

Fuchtenbusch M et al: "Prevention of type 1 diabetes", Medizinische Welt 20030501 DE, vol. 54, No. 5, May 1, 2003, pp. 105-108— Translated summary.

HSP THERAPY IN CONJUNCTION WITH A LOW ANTIGENICITY DIET

CROSS REFERENCE TO RELATED APPLICATIONS

This application is a continuation of application Ser. No. 12/392,862 filed Feb. 25, 2009 which is a divisional of application Ser. No. 11/495,919 filed Jul. 27, 2006, now abandoned, which is a continuation of International application PCT/IL2005/000100 filed Jan. 27, 2005, which claims the benefit of provisional application 60/539,330 filed Jan. 28, 2004. The entire content of each prior application is expressly incorporated herein by reference thereto.

FIELD OF THE INVENTION

The invention relates to methods for delaying the onset of autoimmune diseases, particularly Type 1 diabetes, using administration of a fragment of heat shock protein (HSP), particularly DiaPep277 derived from Hsp60, in conjunction with a low antigenicity diet, particularly a diet comprising hydrolyzed casein, and to methods useful for prevention, delay, suppression or treatment of autoimmune diseases using oral administration of DiaPep277. The present invention further relates to formulations adapted for oral administration of DiaPep277 and other hsp60 peptide analogs and fragments.

BACKGROUND OF THE INVENTION

Type 1 diabetes (also known as insulin dependent diabetes mellitus, IDDM) is an autoimmune disease that results from the destruction of the beta-cells in the pancreas. Environmental factors, such as diet and bacterial antigens play an important role in the onset of the disease (Scott F W, 1996, Diabetes Metab. Rev. 12, 341-359; Scott F W et al., 2002 Diabetes 51, 73-78; Visser J. et al., 2003, Metabolism 52, 333-337).

The immune response of the gut of the neonate is less well-developed than in adults, and this relative immune deficiency makes it easier to induce tolerance to orally administered antigens. The possibility that type 1 diabetes may be related to antigens encountered via the gut lumen has been discussed since the mid-1980s, when evidence first appeared that diet could affect the spontaneous development of diabetes in BB rats and studies in patients implicated early exposure to breast milk substitutes as a risk factor.

Attempts to prevent autoimmune diseases by inducing oral tolerance to selected individual autoantigens have met with mixed success in animals and humans (Gale A. E. 2000, Lancet 356, 526-527).

The diabetogenic factor of the milk appears to be in the casein fraction, at list in the non-obese diabetic (NOD) mice, although other proteins were suggested. It was reported (Virtanen et al. 1993, Diabetes 42 1786-1790) that early introduction of dairy products is associated with increased risk of type 1 diabetes in Finnish children. The most consistently diabetogenic diet in animal models for type 1 diabetes is the commercial, cereal/plant-based rodent diet. In contrast, hydrolyzed casein (HC) diet, in which the sole protein source is hydrolyzed casein, has a protective effect. For instance, it was shown that feeding diabetes-prone bio-breeding rats (BB-DP rats), a HC-diet reduced the diabetic incidence by 30-50% (Visser J. et al., 2003 ibid). Suggested mechanisms for this effect are an actively induced protection against the development of diabetes or avoiding exposure to diabetogenic substances present in plant-based rodent diet. Scott and colleagues reported that the effect of plant-based diet on diabetes was dose-dependent, demonstrating that the diabetogenic load of the diet is important (Scott F W et al., 1997, Diabetes 46, 589-598). Moreover, Li et al. reported hyperexpression of MI-IC class I antigens on beta cells in plant-based diet fed BB-DP rats (Li X-B et al., 1995, Diabetologia 38, 1138-1147). Furthermore, BB-DP rats receiving HC diet from weaning displayed a shift from a Th1 cytokine pattern to a Th2 cytokine pattern in the pancreas at 70 days. Accordingly, when BB-DP rats were weaned on the control diet and after the age of 50 days switched to a HC diet there was an increase in Th2 cytokines in the pancreas, but interferon gamma levels were not affected. Taken together, it seems that some food ingredients can elicit a Th1-response in the pancreas which could lead to destruction of the beta cells, that is prevented by the HC diet.

Various self-antigens have been suggested to play a role in the development of diabetes. Indeed, antibodies against glutamic acid decarboxylase (GAD), insulin, islet cell antigen (ICA-69), and hsp60 have been found in the circulation at the onset of diabetes in humans (Cohen I R 2002, Diabetologia 45, 1468-1474, Yoon J W and Jun H S, 2001, Annals of the NY academy of sciences 928, 200-211), and in pre-diabetic NOD-mice (Brudzynski, 1993, Diabetes 42, 908-13.) and BB rats. Furthermore, antibodies against bacterial hsp65 cross-react with self (human or murine) hsp60. Recent reports have shown that hsp60 molecules also reside within insulin vesicles in the islets. As a result of stress heat shock proteins are synthesized in increased amounts to refold misfolded proteins.

Environmental factors were suggested in the early eighties as trigger for Type 1 Diabetes. The evidence that this environmental trigger is to be found in cow's milk is based on epidemiological (Leslie & Elliott 1994, Diabetes 43, 843-850), ecological (Virtanen et al, 1993, Diabetes 42, 1786-1790) and animal experimental evidence (Elliott & Martin, 1984, Diabetologia 26, 297-299). The diabetogenic factor of the milk appears to be in the casein fraction, at least in the non-obese diabetic (NOD) mouse. Whey protein does not appear to contain any diabetogenic component. It has been suggested that bovine serum albumin (BSA), is the diabetogenic component of cows milk. However, a review of the evidence supporting this theory does not indicate that BSA was ever tested for diabetogenic activity in the absence of β-casein.

Latent autoimmune diabetes in adults (LADA) is a special form of diabetes, which could represent a late manifestation of type 1 diabetes. The immune destructive process is much slower, making it sometimes difficult to distinguish clinically between type 1 and type 2 diabetes. The frequency of LADA patients among all patients diagnosed as type 2 varies between 6-50% in various populations. The frequency is higher in younger age groups. Most of the LADA patients will require insulin within three years. It is still unclear whether early treatment with insulin is beneficial for the remaining beta cells.

International PCT Application WO 95/10537 discloses a method of producing denatured bovine serum albumin milk products. It is stated that the consumption of denatured BSA milk products tends to reduce the likelihood of a person acquiring type 1 diabetes. However, there is no evidence presented of any trials where either human or animal subjects were fed milk or milk products with denatured BSA. It relies upon the theory mentioned above that BSA is the diabetogenic component of cows' milk.

U.S. Pat. No. 6,451,368 discloses a method for selecting non-diabetogenic milk or milk product based on the finding that specific variant of casein has diabetogenic activity while another variant does not have. The disclosure shows that antibodies to mixed caseins are found at higher levels in newly diagnosed diabetics than in normal controls.

U.S. Pat. No. 6,451,552 discloses a method for selective production of a casein/caseinate hydrolysate stripped of immunogenic proteins by treating milk with a protease that selectively hydrolyzes casein and subsequent separating the hydrolysed casein from unhydrolyzed immunogenic protein by membrane ultrafiltration. The inventors claim that the resulting hydrolyzate is essentially free of antigenic components of the ABBOS peptide and bovine serum albumin.

Elias et al. (1997, 46, 758-64.) demonstrated a specific peptide of human hsp60, p277, to be one of the immunodominant epitopes in autoimmune diabetes. Accordingly, T-cell reactivity to p277 has been reported at the onset of diabetes in NOD mice. Interestingly, subcutaneous administration of p277 downregulated T-cell reactivity to beta cell antigens and prevented the development of diabetes in NOD mice. Treatment induced p277-specific IgG1 antibodies as well as an increase in p277-specific IL-4 and IL-10 secretion and a decrease in gamma interferon secretion, suggesting an upregulation of the Th2 cytokine pathway. The destruction of the islets of Langerhans in the pancreas is believed to be a Th1 response. A shift of Th1 to Th2 response caused by p277 could be the cause of the attenuation of diabetes.

Heat shock proteins (HSPs) are highly conserved proteins expressed in all pro- and eukaryotic cells. They are involved in many important cellular processes such as correct folding of newly synthesized proteins and subunit assembly and therefore are termed molecular chaperones (Bukau, B., et al. 2000, Cell 101, 119-122). Under non-physiological conditions like high temperature, ultraviolet radiation, a viral or bacterial infection, cellular HSP synthesis is up-regulated. HSPs exert cytoprotective functions such as preventing the aggregation of denatured proteins, initiating their refolding or proteolytic degradation (Singh-Jasuja, H., et al. 2001, Biol. Chem. 382, 629-636). According to their molecular weight, HSPs are divided into six subfamilies: small HSPs, HSP40, HSP60, HSP70, HSP90 and HSP100. They are located in the cytosol (HSP70, HSP90, HSP100), in the endoplasmic reticulum (HSP70, HSP90) or in mitochondria (HSP60).

Recently, the HSP60, HSP70, and HSP90 subfamilies have attracted increasing attention because of their potential roles in immunologically relevant processes. Several studies have identified HSPs as targets of immune responses during microbial infections (Zugel, U., and Kaufmann, S. H., 1999, Immunobiology 201, 22-35). Because of the high sequence homology between microbial FISPs and endogenous HSPs derived from damaged or stressed tissue, immunological cross-reactivity was suggested to contribute to the development of autoimmune disorders including rheumatoid arthritis and diabetes (Holoshitz, J., et al. 1986, Lancet 2, 305-309; Elias, D., et al., 1991, Proc. Natl. Acad. Sci. U.S.A 88, 3088-3091; Abulafia-Lapid, R., et al., 1999, J. Autoimmun. 12, 121-129).

Hsp60 is a mitochondrial chaperone with a major role in protein folding and unfolding as well as translocation of proteins into mitochondria. Hsp60 is found in the cell cytosol under stressful and inflammatory conditions; infection or elevated cytokine levels will induce the cellular stress response. Therefore, it is not surprising that hsp60 is a highly immunogenic protein: it is the "common antigen" of gram-negative bacteria. Immunological reactivity to both bacterial and autologous-hsp60 is highly prevalent in the general population, since the pathogen-directed immune response can easily convert into an autoimmune response due to the high homology.

T-cell responses to multiple hsp60 epitopes are present in various autoimmune and inflammatory diseases including type 1 diabetes, rheumatoid and juvenile arthritis, multiple sclerosis, ankylosing spondylitis, pelvic inflammation-associated infertility, inflammatory bowel disease, atherosclerosis, graft rejection and more. The immune system reacts to hsp60 epitopes that are either cross-reactive between the human and bacterial analogues, or idiosyncratic.

Many disclosures claim uses of heat shock proteins or fragments thereof as immune modulators in diagnosis, treatment or prevention of autoimmune diseases. Most of these disclosures relate to heat shock protein 60 also known previously as hsp65, or fragments of this protein. Antibodies against the 60 kDa heat shock protein 60 (hsp60), which have a high homology to bacterial hsp65, have been found in the circulation at the onset of diabetes in humans and in pre-diabetic NOD-mice.

For example, the particular protein produced by the human body during development of type 1 diabetes, which serves as a diagnostic marker for the incipient outbreak of type. 1 diabetes, is the human heat shock protein having a size of about 65 KD (human hsp65) or an antigen cross-reactive therewith as disclosed in EP 0417271, and in U.S. Pat. Nos. 5,114,844; 5,671,848; 5,578,303 and 5,780,034. It has been disclosed that fragments of this hsp60 protein may serve as therapeutically useful entities in preventing or alleviating type 1 diabetes and host vs. graft disease (U.S. Pat. Nos. 6,180,103 and 5,993,803 and WO 96/19236, WO 97/01959 and WO 98/08536).

The peptide p277 corresponding to positions 437-460 of human Hsp60 was discovered to be one of the immunodominant epitopes in autoimmune diabetes. Its analog, denoted DiaPep277™, disclosed in U.S. Pat. No. 6,180,103 and WO 96/19236 as p277(Val$^6$, Val$^{11}$) is a synthetic peptide analog of p277, in which two cystein residues at positions 6 and 11 were replaced with Valine residues. Nowhere in the prior art it is shown that DiaPep277 can be effective after oral administration and nowhere in the prior art it was shown or suggested that administration of DiaPep277 together with hydrolysed casein diet may positively influence the progress or outcome of diabetes.

An experimental study presented by the inventors of the present application is described in Brugman et al. 2004, Diabetologia, 1331-1333.

There is an unmet need to provide orally effective compositions for prevention, delay, suppression and treatment of diabetes. The present invention fulfils this need by providing orally active fragments and analogs of hsp60 and methods for improving the protective effect of a low antigenicity diet such as a hydrolyzed casein diet.

SUMMARY OF THE INVENTION

The present invention provides a method for improvement of the protective effect of a hydrolyzed protein/low antigenicity diet by administration of a fragment of hsp60 or an analog thereof.

The present invention further provides a method for suppression, prevention or treatment of diabetes, particularly type 1 diabetes (IDDM), comprising administering a fragment of Hsp60 or analog thereof in conjunction with a low antigenicity diet, particularly hydrolyzed casein (HC) diet.

The present invention further provides a method for suppression, prevention or treatment of latent autoimmune diabetes in adults (LADA) which is classified as a sub-type of type 1 diabetes, comprising administering a fragment of Hsp60 or analog thereof in conjunction with a low antigenicity diet, particularly hydrolyzed casein (HC) diet.

According to the present invention, casein or other proteins which are diabetogenic may be omitted from the patient's diet or replaced with a hydrolyzed or denatured form and be given to the patient in a low antigenicity diet in conjunction with the administration of a Hsp60 fragment or analog. A non-limitative list of proteins which are suspected to be diabetogenic and therefore may be avoided or replaced with a hydrolyzed or denatured form, according to the principles of the present invention are: casein, lactoglobulin, albumin, (pro)insulin, wheat gluten, soy bean proteins, and bacterial antigens such as Hsp60.

According to a specific embodiment of the present invention, casein hydrolysate is the main protein source in the diet while according to another embodiment the casein hydrolysate is substituted by whey hydrolysate, casein/whey hydrolysate, soy hydrolysate, and mixtures thereof. According to yet another embodiment of the present invention the protein source of a patient's diet is replaced by free amino acids, short-chain peptides, or a mixture thereof.

Preferably the hsp60 fragment comprises residues 437-460 of hsp60 having the sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp (SEQ ID NO:1). More preferably it is a Val$^6$,Val$^{11}$ analog of residues 437-460 of Hsp60 comprising the sequence of SEQ ID NO:2:

```
                                                            (SEQ ID NO: 2)
1                   6                  11
Val-Leu-Gly-Gly-Gly-Val-Ala-Leu-Leu-Arg-Val-Ile-Pro-Ala-Leu-Asp-Ser-Leu-Thr-Pro-

24
Ala-Asn-Glu-Asp,
herein denoted DiaPep277.
```

According to another embodiment, the Hsp60 fragment peptide used in conjunction with a hydrolyzed casein diet in a method for suppression, prevention or treatment of diabetes, particularly type 1 diabetes, is selected from the group consisting of:

```
residues 31-50 of human Hsp60:
                                     (SEQ ID NO: 3)
Lys-Phe-Gly-Ala-Asp-Ala-Arg-Ala-Leu-Met-Leu- Gln-Gly-Val-Asp-Leu-Leu-Ala-Asp-Ala;

(SEQ ID NO: 4)
residues 136-155 of human Hsp60:
Asn-Pro-Val-Glu-Ile-Arg-Arg-Gly-Val-Met-Leu- Ala-Val-Asp-Ala-Val-Ile-Ala-Glu-Leu;

residues 151-170 of human Hsp60:
                                     (SEQ ID NO: 5)
Val-Ile-Ala-Glu-Leu-Lys-Lys-Gln-Ser-Lys-Pro- Val-Thr-Thr-Pro-Glu-Glu-Ile-Ala-Gln;

residues 166-185 of human Hsp60:
                                     (SEQ ID NO: 6)
Glu-Glu-Ile-Ala-Gln-Val-Ala-Thr-Ile-Ser-Ala- Asn-Gly-Asp-Lys-Glu-Ile-Gly-Asn-Ile;

residues 195-214 of human Hsp60:
                                     (SEQ ID NO: 7)
Arg-Lys-Gly-Val-Ile-Thr-Val-Lys-Asp-Gly-Lys- Thr-Leu-Asn-Asp-Glu-Leu-Glu-Ile-Ile;

residues 255-274 of human Hsp60:
                                     (SEQ ID NO: 8)
Gln-Ser-Ile-Val-Pro-Ala-Leu-Glu-Ile-Ala-Asn- Ala-His-Arg-Lys-Pro-Leu-Val-Ile-Ile;

residues 286-305 of human Hsp60:
                                     (SEQ ID NO: 9)
Leu-Val-Leu-Asn-Arg-Leu-Lys-Val-Gly-Leu-Gln- Val-Val-Ala-Val-Lys-Ala-Pro-Gly-Phe;

residues 346-365 of human Hsp60:
                                     (SEQ ID NO: 10)
Gly-Glu-Val-Ile-Val-Thr-Lys-Asp-Asp-Ala-Met- Leu-Leu-Lys-Gly-Lys-Gly-Asp-Lys-Ala;

residues 421-440 of human Hsp60:
                                     (SEQ ID NO: 11)
Val-Thr-Asp-Ala-Leu-Asn-Ala-Thr-Arg-Ala-Ala- Val-Glu-Glu-Gly-Ile-Val-Leu-Gly-Gly;

residues 436-455 of human Hsp60:
                                     (SEQ ID NO: 12)
Ile-Val-Leu-Gly-Gly-Gly-Cys-Ala-Leu-Leu-Arg- Cys-Ile-Pro-Ala-Leu-Asp-Ser-Leu-Thr;

residues 466-485 of human Hsp60:
                                     (SEQ ID NO: 13)
Glu-Ile-Ile-Lys-Arg-Thr-Leu-Lys-Ile-Pro-Ala-Met- Thr-Ile-Ala-Lys-Asn-Ala-Gly-Val;

residues 511-530 of human Hsp60:
                                     (SEQ ID NO: 14)
Val-Asn-Met-Val-Glu-Lys-Gly-Ile-Ile-Asp-Pro- Thr-Lys-Val-Val-Arg-Thr-Ala-Leu-Leu;

residues 343-366 of human Hsp60:
                                     (SEQ ID NO: 15)
Gly-Lys-Val-Gly-Glu-Val-Ile-Val-Thr-Lys-Asp- Asp-Ala-Met.
```

According to another aspect the present invention provides a regimen for delaying the onset of type 1 diabetes and for inhibition of insulitis, comprising:
i. administering of human hsp60 fragment or analog; and
ii. maintaining a HC diet.

According to one embodiment the human hsp60 fragment is p277 (SEQ ID NO:1) or its analog DiaPep277 (SEQ ID NO:2) and the administration is oral. According to another embodiment the human hsp60 fragment is selected from the group consisting of SEQ ID NOS:3-15. According to yet another embodiment, the administration of said fragment or analog is nasal or bronchial.

According to another aspect the present application provides compositions and methods for potentiating the protective effect of hydrolyzed casein-diet.

According to another aspect the present invention provides methods for oral administration of Hsp60 fragments and analogs. According to a preferred embodiment the peptide comprises residues 437-460 of human Hsp60 (SEQ ID NO:1). According to a most preferred embodiment the peptide is DiaPep277 which is a Val$^6$, Val$^{11}$ analog of residues 437-460 of human Hsp60, of SEQ ID NO:2. According to other embodiments the human hsp60 fragment is selected from the group consisting of SEQ ID NOS:3-15.

A preferred embodiment provides methods of treating an individual in need thereof by administering a pharmaceutical composition comprising a fragment of a heat shock protein or an analog thereof in conjunction with a hydrolyzed protein/low antigenicity diet.

These pharmaceutical compositions are preferably administered by oral, nasal or bronchial routes, although other routes of administration, including topical, transdermal or systemical are possible and are within the scope of the present invention if they result in improvement of the protective effect of a hydrolyzed protein/low antigenicity diet.

BRIEF DESCRIPTION OF THE DRAWINGS

The invention will better be understood in relation to the drawings and detailed description of the preferred embodiments which follow.

DETAILED DESCRIPTION OF THE INVENTION

Terminology and Definitions

Figure 1:
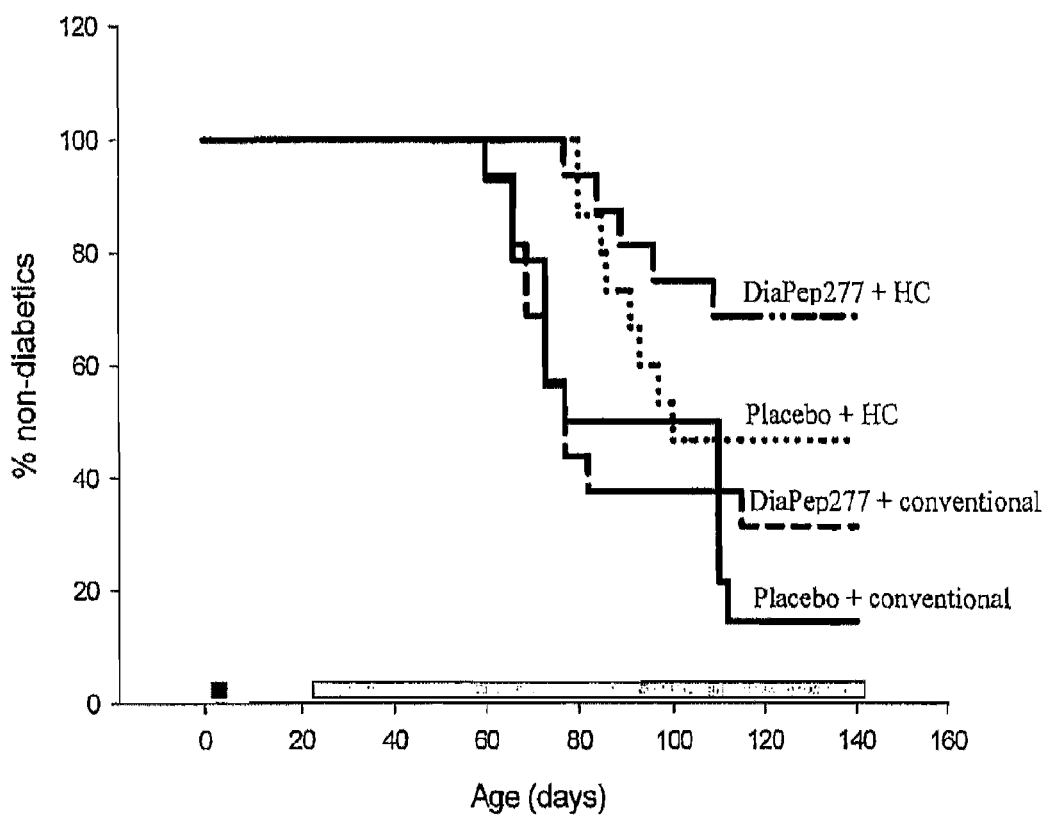
FIG. 1: Describes the diabetes incidence of treated BB-DP rats following administration of DiaPep277 or placebo together with conventional or hydrolyzed casein diet. Bold line: placebo+conventional diet (n=14); broken bold line: placebo+HC-diet (n=15); broken line with single dots: DiaPep277+conventional diet (n=16); broken line with double dots: DiaPep277+HC-diet (n=16).

The term "heat shock protein" relates to any member of heat shock proteins family also known as chaperones. The term "heat shock protein" also referred to "stress protein" a term that was used in the past to such molecules.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "analog" further indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted.

An "effective peptide" will have the activity to achieve a desired result, such as cytokine inhibition or induction. Alternatively, an effective peptide will provide the cell with a beneficial or therapeutic effect, such as induction of release of a specific mediator. Thus reference to a particular peptide or "analog" includes the naturally occurring peptide sequence or a peptide that has the substantially the same activity as the naturally occurring sequence. "Effective peptides" of the invention also include modified peptides (with amino acid substitutions, both conservative and non-conservative) that have the same activity as a wild-type or unmodified peptide. "Salts" of the peptides of the invention contemplated by the invention are physiologically acceptable organic and inorganic salts.

As used herein and in the claims, the phrase "therapeutically effective amount" means that amount of peptide or peptide analog or composition comprising same to administer to a host to achieve the desired results for the indications disclosed herein.

The term "hydrolyzed casein" or "hydrolyzed protein" means that the intact protein is hydrolyzed into peptide fragments whereby a majority of peptides fragments have a molecular weight of less than 1000 Daltons. Free amino acids and synthetic short peptide chains may also be either substituted for or added to the protein hydrolysates as the nitrogen source so long as the nutritional composition has an amino acid profile suitable for the targeted population, as within the skill of one familiar with the art of nutritional formulations. The amount of protein employed in the nutritional composition may be determined by the nutrient profile targeted for a specific formulation, as well known to those skilled in the art. The protein source of a diet according to the present invention may be selected from any appropriate nitrogen sources, such as, extensively hydrolyzed protein, free amino acids, short-chain peptides and mixtures thereof appropriate for formulation of elemental diet compositions. The actual amino acid/peptide content will depend upon the desired nutritional goals of the particular composition. Favored proteins include hydrolyzed protein hydrolysates prepared from acid or enzyme treated animal and vegetable proteins, such as, casein hydrolysate, whey hydrolysate, casein/whey hydrolysate, soy hydrolysate, and mixtures thereof.

The term "insulitis" relates to inflammation of the islands of Langerhans, with lymphocytic infiltration. Insulitis may result from different stimuli including viral infection and it is the initial lesion leading to type 1 diabetes.

Certain abbreviations are used herein to describe this invention and the manner of making and using it. For instance, BB-DP refers to diabetes-prone bio-breeding, BSA refers to bovine serum albumin, GAD refers to Glutamic acid decarboxylase, GIT refers to gastro-intestinal tract, HC refers to hydrolyzed casein, Hsp refers to heat shock protein, ICA refers to islet cell antigen, IDDM refers to Insulin-dependent Diabetes Mellitus, IL—refers to interleukin, NOD refers to non-obese diabetic.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It was now surprisingly found that the combination of DiaPep277 and HC diet reduces the diabetes incidence dramatically in BB-DP rats. This protection correlates with a total lack of insulitis, in the non-diabetic animals, suggesting that protection from diabetes occurs at the level of the pancreatic beta-cells. In contrast, non-diabetic animals in all other groups display a mild form of insulitis. Thus, only the combination of Diapep277 and HC-diet completely prevents development of insulitis in the islets.

Several research groups have reported that FIC-diet has a protective effect on the development of diabetes in the BB-DP rat (Scott F W, 1996, Visser J., et al. 2003, Scott F W et al. 1997, Li X-B et al. 1995). It was now confirmed that HC-diet delays the onset of the disease by 17-20 days and reduces the diabetes incidence. Protection against diabetes by HC-diet could be the result of an actively induced protective mechanism or could be the result of not exposing rats to diabetogenic substances present in plant-based rodent diets. However, preliminary data show that HC-diet also modifies the composition of the intestinal flora (Brugman et al., manuscript in preparation). The intestinal bacterial flora is important in constituting tolerance to commensals and food ingredients and disturbance of this process could have a profound effect on the development of autoimmunity.

BB-DP rats were orally inoculated once per day with either placebo (aqua dist.) or DiaPep277 at day 4, 5, 6 and 7 of life. At the age of 21 days rats were weaned either on a conventional, cereal-based diet or on the hydrolyzed casein-diet. Animals receiving DiaPep277 in combination with HC-diet showed a delay in the development of diabetes of 17 days, a reduction of the incidence by 54% (compared to the group receiving placebo and conventional-diet) and a total lack of insulitis in the non-diabetic animals. Short-term neonatal feeding with DiaPep277 in early life combined with diet adaptation appears to provide a safe procedure to significantly reduce type 1 diabetes development in later life.

The sequence of bacterial hsp65 has a high homology with human and rat hsp60. It has been reported that hsp60 is present in secretory insulin granules and on the cell surface of beta-cells (Brudzynski K, 1993). An immune response to hsp65 could lead to an autoimmune response to hsp60 on beta-cells on the basis of molecular mimicry. Neonatal oral introduction of one of the epitopes of hsp60 could lead to tolerance to this epitope, reducing the risk of molecular mimicry induced auto-immunity, and thereby establishing protection at the level of the pancreatic beta cells. Neonatal administration of Diapep277 alone did not lead to significant protection against diabetes. However, plant-based diets probably contain many more diabetogenic substances which can evoke an immune response. Most likely the overload of these other diabetogenic epitopes masks the tolerance established for hsp60 and related proteins through oral administration of Diapep277. Using a non-diabetogenic HC diet could well eliminate the masking effect. Alternatively, the additive protective effect of the HC-diet to Diapep277 treatment could be indirect. Since intestinal bacteria are a major source of hsp65, changes in the bacterial flora could change the amount of epitopes with a high homology to self antigens, and therefore affect the development of autoimmunity. Obviously, a combination of the two mechanisms is also possible.

As disclosed herein for the first time, it was shown that combining neonatal oral administration of Diapep277 with a non-diabetogenic diet from weaning on leads to a dramatic decrease in the diabetes incidence and a delay in the onset of the disease in BB-DP rats. Moreover, such non-diabetic rats are completely protected from beta-cell auto-reactivity, as shown by the complete absence of insulitis in these animals. Short-term neonatal feeding with DiaPep277 in early life combined with diet adaptation appears therefore to provide a clinically relevant and safe procedure to significantly reduce type 1 diabetes development later in life.

Routes of Administration

It is known that injections are associated with disadvantages. Thus, for example, lipodystrophy or other foreign body reactions can occur at the administration site. Problems with the handling of injection syringes are particularly to be expected with very young and relatively old patients. In these groups of patients, a regularly required injection must often be carried out by a person looking after them. It is therefore obvious that this effort does not particularly promote patient compliance.

The optimum, simplest and safest use of pharmaceutical substances, however, is oral administration, for example of tablets, capsules or beverage solutions. In the case of peptide pharmaceutical substances, marked difficulties result, however, because these are inactivated to the greatest part by enzymatic degradation after release in the gastro-intestinal tract (GIT; stomach or small intestine) even before absorption. Enzymatic degradation in the stomach or small intestinal fluid or on the mucosa threatens to lower the bioavailability of peptide pharmaceutical substances, particularly insulin, to a minimum. Additionally, the mechanism of absorption by means of passive transport is largely lacking for peptide pharmaceutical substances. This is based, on the one hand, on the molecular size, because the exclusion limit for passive transport is assumed to be about 500 Daltons. On the other hand, substance-specific properties, such as hydrophilicity (low distribution coefficient), self-association to form larger units or binding to constituents of the gastro-intestinal tract make absorption difficult. According to the present invention an additive effect of DiaPep277 when combined with HC diet suggests that DiaPep277 is not degraded before it has its effect. Additional preferred modes of administration routes are nasal and bronchial which might trigger tolerance induction of mucosal immunity.

HC diet is a modified diet, were the protein source is replaced by hydrolyzed casein. One example for an HC diet is a modification of the AIN-93G diet containing 20% hydrolyzed casein as the source of aminoacids, 53% corn starch, 12% sucrose, 5% corn oil, 5% cellulose-type fiber, and supplemental vitamin and mineral mix (Visser J. et al., 2003, Metabolism 52, 333-337, 4, Scott F W et al., 1997, Diabetes 46, 589-598). Other types of HC diets with different compositions are within the scope of the present invention.

Induction of protection against autoimmune diseases, via oral administration of DiaPep277 can improve the preventive effect of a hydrolyzed protein diet and low antigenicity diet, such as hydrolyzed casein diet. In these diets the antigenic protein is omitted or replaced with an hydrolyzed form. According to the present invention, casein or any other protein which is suspected to be diabetogenic may be omitted from the patient's diet or replaced with hydrolyzed or denatured form and be given to the patient in a diet in conjugation with a Hsp60 fragment or analog. A non-limitative list of proteins which are suspected to be diabetogenic and therefore may be used according to the present invention are: casein, lactoglobulin, albumin, (pro)insulin, wheat gluten, soy bean proteins, and bacterial antigens such as hsp60.

Pharmacology

Apart from other considerations, the fact that the novel active ingredients of the invention are peptides, peptide analogs or peptidomimetics, dictates that the formulation be suitable for delivery of these type of compounds. In general, peptides are less suitable for oral administration due to susceptibility to digestion by gastric acids or intestinal enzymes, but it is now disclosed that the compositions according to the present invention my be preferably administered orally. Other routes of administration according to the present invention are intra-articular, intravenous, intramuscular, subcutaneous, intradermal, or intrathecal.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the fragments and analogs described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In one particularly preferred embodiment according to the present invention, the peptides are administered orally (e.g. as a syrup, capsule, or tablet).

In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy, 1998, Biotechnol. Prog. 14, 108; Johnson et al., 1996, Nature Med. 2, 795; Herbert et al., 1998, Pharmaceut. Res. 15, 357) a dry powder composed of biodegradable polymeric microspheres containing the protein in a polymer matrix that can be compounded as a dry formulation with or without other agents.

The foregoing formulations and administration methods are intended to be illustrative and not limiting. It will be appreciated that, using the teaching provided herein, other suitable formulations and modes of administration can be readily devised. Formulations of the present invention suitable for oral administration may be presented as discrete units such as capsules, cachets, tablets, lozenges comprising the peptide(s) in a flavoured base, usually sucrose and acacia and tragacanth; pastilles comprising the active ingredient(s) in an inert base such as gelatin and glycerin, or sucrose and acacia; and mouth washes comprising the active ingredient(s) in a suitable liquid carrier. Each formulation generally contains a predetermined amount of the active peptide(s); as a powder or granules; or a solution or suspension in an aqueous or non-aqueous liquid such as a syrup, an elixir, an emulsion or draught and the like.

A tablet may be made by compression or moulding, optionally with one or more accessory ingredients. Compressed tablets may be prepared by compressing in a suitable machine the active peptide(s) in a free-flowing form such as a powder or granules, optionally mixed with a binder, (eg povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Moulded tablets may be made by moulding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

A syrup may be made by adding the active peptide(s) to a concentrated, aqueous solution of a sugar, for example, sucrose, to which may also be added any necessary ingredients. Such accessory ingredients) may include flavourings, an agent to retard crystallisation of the sugar or an agent to increase the solubility of any other ingredients, such as a polyhydric alcohol, for example, glycerol or sorbitol.

In addition to the aforementioned ingredients, the formulations of this invention may further include one or more accessory ingredients) selected from diluents, buffers, flavouring agents, binders, surface active agents, thickeners, lubricants, preservatives, (including antioxidants) and the like.

According to some embodiments of the invention, the therapeutically effective amount of the hsp fragment or analog is a dosage in a range from about 0.02 mg/kg to about 10 mg/kg. Preferably, the dosage of the hsp fragment or analog according to the present invention is in a range from about 0.05 mg/kg to about 2 mg/kg, more preferably, the dosage of the hsp fragment or analog is in a range from about 0.1 mg/kg to about 1 mg/kg. It will be understood that the dosage may be an escalating dosage so that low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

EXAMPLES

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the amended claims.

Example 1

Neonatal Oral Administration of DiaPep277 in Combination with the Protective Hydrolyzed Casein Diet Materials and Methods:

Experimental set-up: Group-housed BB-DP rats (breeding colony, Groningen, the Netherlands) were orally inoculated once per day with either placebo (aqua dist.) or Diapep277 at days 4, 5, 6 and 7 of life (black box in FIG. 1). Animals were treated in compliance with the principles of laboratory care (NIH publication no. 85-23, revised 1985) and the Dutch law on experimental animal care. Inoculation was done via a silicon-tube swallowed by the neonate and fluid was inoculated directly into the stomach. DiaPep277 was supplied by Peptor Ltd., Rehovot, Israel. It is an analog of the native 437-460 sequence of human hsp60, in which the existing cystein residues at positions 442 and 447 were replaced by valine, for better chemical stabilization. Per inoculation 300 µg/rat of Diapep277 in a volume of 300 µl was administered. At the age of 21 days (gray box in FIG. 1) rats were weaned either on a conventional, cereal-based diet (Hope Farms, rodent diet no. Rmh-B2181, Woerden, Netherlands) or on HC-diet, a modification of the AIN-93G diet containing 20% hydrolyzed casein (Pancase S; Redstar Bioproducts, Tara, Canada) as the source of aminoacids, 53% corn starch, 12% sucrose, 5% corn oil, 5% cellulose-type fiber (Solka-Floc; Teklad, Madison, Wis.) (Visser J. et al., 2003, Metabolism 52, 333-337, Scott F W et al., 1997, Diabetes 46, 589-598). In this study both sexes were used. In our colony 80% to 90% of the BB-DP rats spontaneously develop diabetes before the age of 130 days, with no gender differences. Body weights were measured three times per week. In case of weight loss the animal was screened for hyperglycemia, using blood glucose strips (Roche diagnostics, Almere, Netherlands). Rats were diagnosed as diabetic at plasma glucose above 15 mmol/L. Non-diabetic animals were sacrificed at the end of the study, at the age of 140 days. Histopathology: Upon necropsy, the pancreas was removed, fixed in Bouin's solution, and after washing, embedded in paraffin. Sections of 7 µm were stained with hematoxylin/eosin for evaluation of insulitis. The degree of islet infiltration was measured using a Zeiss microscope and was rated as previously described (Visser J. et al., 2003, Metabolism 52, 333-337) with the addition of score 5 which is developed in our lab, to control for completely destroyed islets in severe insulitis. Per pancreas section, an average histological insulitis score was calculated by adding up the score of each islet and dividing it by the total number of islets counted. The analysis was performed blindly and independently by two persons.

Results:

As shown in FIG. 1, administration of neonatal DiaPep277 combined with a conventional rodent diet from weaning tended to lower the diabetes incidence in BB-DP rats from 85% (placebo+conventional) to 69% (DiaPep277+conventional), and from 53% (placebo+HC) to 31% (DiaPep277+HC) respectively, although these differences were not significant. The HC-diet delayed the onset of diabetes by 20 days and tends to lower the incidence of diabetes by 33% (Kaplan Meier, p=0.06).

Animals receiving DiaPep277 in combination with HC-diet have both a delay in the development of diabetes of 17 days and a lower diabetes incidence. In this group only 31% of the animals became diabetic, a decrease of 54% compared to control (Kaplan Meijer; p=0.0034 vs. placebo+conventional diet). All animals receiving DiaPep277 have a 2.2 fold improved change of not developing diabetes (endpoint analysis, $\chi^2$).

Figure 2:
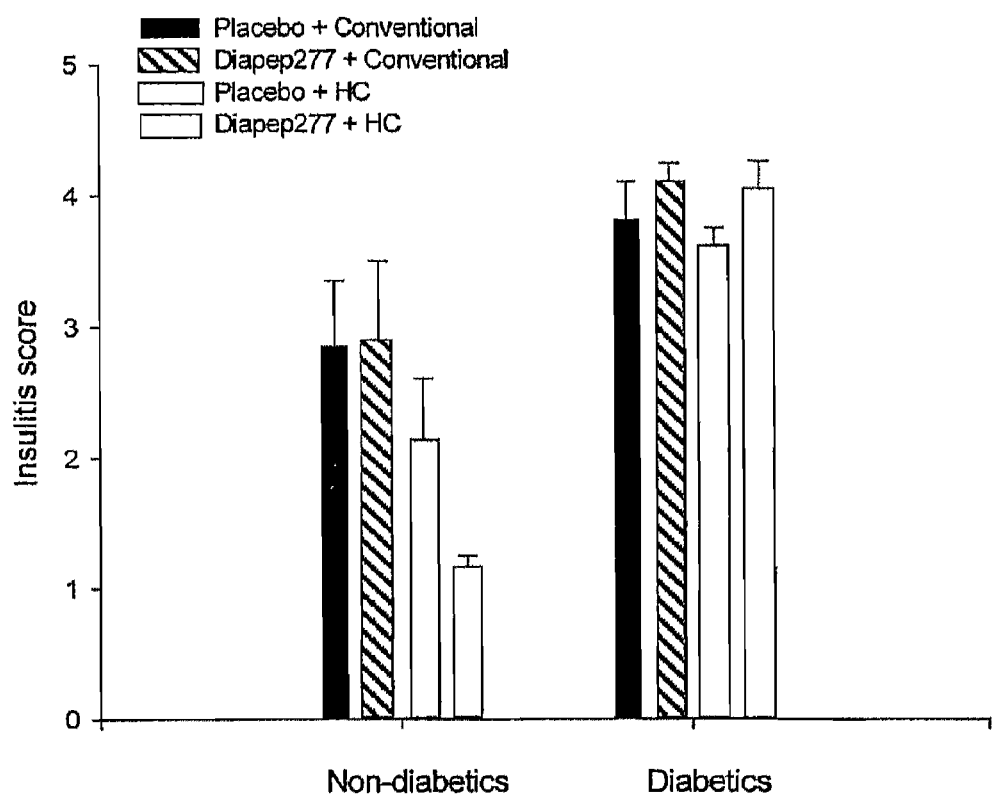
FIG. 2: Illustrates the insulitis score of non-diabetic and diabetic rat following administration of DiaPep277 or placebo together with conventional or hydrolyzed casein diet. Black bars: placebo+conventional diet (n=14); hatched bars: DiaPep277+conventional diet (n=16); gray bars: placebo+HC diet (n=15); white bars: Diapep277+HC diet (n=16). Scores: 1—normal islet appearance; 2—mild insulitis; 3—severe insulitis; 4—end-stage islets; 5—missing islets as compared to the average number of islets in the normal rat pancreas.

The insulitis score of the different groups is depicted in FIG. 2 (score 1: normal islet appearance, score 2: mild insulitis, score 3: severe insulitis, score 4: end-stage islets, score 5: missing islets as compared to the average number of islets in the normal rat pancreas). Interestingly, combination of neonatal administration of Diapep277 followed by the HC-diet from weaning resulted in a dramatic reduction of insulitis in the non-diabetics, e.g. score around 1.0 (Wilcoxon Signed Rank, p=0.043 compared with placebo/conventional-diet), comparable with scores found in healthy BB-DP rats and diabetes-resistant BB rats (BB-DR) with normal islet appearance Example 2

Dose Response Effect of Oral Administration of DiaPep277 on the Development of Diabetes Type 1 in the BB-DP Rat It was shown that neonatal oral administration of DiaPep277 in combination with the protective HC diet significantly delayed the onset of diabetes type 1 in the 13B-DP rat and decreased the incidence by 64% compared to placebo controls on a conventional diet. Administration of DiaPep277 in combination with a conventional diet tended to lower the incidence. Instead of 85% only 69% of the animals became diabetic. In this previous experiment orally DiaPep277 was administered on four consecutive days (day 4, 5, 6, and 7 of life) in a concentration of 300 µg/rat/day. Since this dose by itself tended to lower the diabetes incidence a dose response experiments are performed to check whether the effect of DiaPep277 becomes more pronounced at higher doses and whether a prolongation of the administration period (longer than four consecutive days) also increases the effect of DiaPep277.

Materials and Methods:

Six groups of BB-DP rats are orally administered with DiaPep277 or Placebo (PBS) from day 4 till day 14 as described in table 1.

TABLE 1

Different treatment groups.

| Number of rats | Dose of DiaPep277 µg/rat |
|---|---|
| 10 | 300 |
| 10 | 450 |
| 10 | 600 |
| 4 | PBS (300 µl) |
| 4 | PBS (450 µl) |
| 4 | PBS (600 µl) |

Three control groups are included. After 21 days rats receive conventional diet and are monitored till the age of 150 days. If an animal loses weight, blood glucose is determined. If the blood glucose level exceeds 15 mM, rats are considered diabetic and the pancreas is removed to determine the level of insulitis. At 150 days the non-diabetic animals are sacrificed and the insulitis score is determined.

Based on the results the dose of DiaPep277 showing optimal effect on reducing and/or delaying the inset of diabetes in the rats is chosen as "preventive dose" and a second study is performed. In this study, the preventive dose or control (PBS) is administered on days 4-14 to large groups of rats (30 per treatment arm), and followed up for signs of diabetes, as above. In addition, five rats of each group are sacrificed at 2 weeks, 1, 2, 3, 4 and 5 months of age, and at each time point the spleen is removed to determine the cytokine profile. Determination of the cytokine profile is performed by subjecting the spleen-derived lymphocytes to the following stimuli: None; Concanavalin A (1 microgram/ml); DiaPep277 (5 microgram/ml); DiaPep277 (25 microgram/ml). Concanavalin A is a non-selective activator of T lymphocytes and demonstrate the non-specific cytokine profile, while the DiaPep277 stimulation, at different concentrations, indicates how the preventive treatment changed the specific cytokine response. While the non-specific stimulus produces similar results in control and DiaPep277 treated rats, the DiaPep277 stimulation shows a focused Th2/Treg response in the splenocytes from DiaPep277-treated rats.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A method for suppression, prevention, delaying the onset or treatment of diabetes by inhibition of insulitus, comprising orally administering to an individual in need thereof a therapeutically effective amount of an active agent consisting of a fragment of Hsp60 or analog thereof in aqueous solution, in conjunction with a low antigenicity diet wherein a diabetogenic protein is replaced with a hydrolyzed or denatured form of the protein, wherein the fragment of Hsp60 or analog thereof consists of residues 437-460 of hsp60 having the sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp (SEQ ID NO:1) or DiaPep277 having the sequence: Val-Leu-Gly-Gly-Gly-Val-Ala-Leu-Leu-Arg-Val-Ile-Pro-Ala-Leu-Asp-Ser-Leu-Thr-Pro-Ala-Asn-Glu-Asp (SEQ ID NO:2), or a salt or functional derivative thereof, and wherein the Hsp60 fragment or analog is administered in a dosage ranging from about 0.1 mg/kg to about 10 mg/kg.

2. The method of claim 1, wherein the low antigenicity diet is maintained for duration of at least 119 days.

3. The method according to claim 1, wherein the diabetogenic protein replaced is selected from the group consisting of: casein, lactoglobulin, albumin, (pro)insulin, wheat gluten, soy bean proteins, and heat shock proteins.

4. The method according to claim 1, wherein the hydrolyzed protein is selected from the group consisting of: casein hydrolysate, whey hydrolysate, soy hydrolysate, or a mixture thereof.

5. The method according to claim 1, wherein the hydrolyzed protein is hydrolyzed casein.

6. The method according to claim 1, wherein the protein source of the diet is replaced with free amino acids, short-chain peptides, or mixtures thereof.

7. The method according to claim 1, wherein the diabetes is type 1 diabetes.

8. The method according to claim 1, wherein the diabetes is latent autoimmune diabetes in adults (LADA).

9. The method according to claim 1, wherein the Hsp60 fragment or analog is administered by a route of administration selected from oral, nasal, bronchial, topical, transdermal and systemic administration.

10. The method according to claim 1, wherein the Hsp60 fragment or analog is administered orally.

11. The method according to claim 1, wherein the Hsp60 fragment or analog is formulated for oral administration.

12. The method according to claim 1, wherein the diabetes is type 1 diabetes and the diet comprises hydrolyzed casein diet.

13. A method for suppressing diabetes which comprises orally administering to an individual in need thereof a therapeutically effective amount of an active agent consisting of an analog of Hsp60 in aqueous solution, in conjunction with a low antigenicity diet wherein a diabetogenic protein is replaced with a hydrolyzed or denatured form of the diabetogenic protein; wherein the analog of hsp60 is residues 437-460 of hsp60 having the sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp (SEQ ID NO:1), DiaPep277 having the sequence: Val-Leu-Gly-Gly-Gly-Val-Ala-Leu-Leu-Arg-Val-Ile-Pro-Ala-Leu-Asp-Ser-Leu-Thr-Pro-Ala-Asn-Glu-Asp (SEQ ID NO:2), or a salt or functional derivative thereof, and wherein the Hsp60 fragment or analog is administered in a dosage ranging from about 0.1 mg/kg to about 10 mg/kg.

14. The method of claim 13, wherein the low antigenicity diet is maintained for duration of at least 119 days.

15. The method according to claim 13, wherein diabetes is suppressed by inhibition of insulitis.

16. The method according to claim 13, wherein diabetes is suppressed by inhibition of insulitis.

* * * * *

SEQUENCE LISTING

<160> NUMBER OF SEQ ID NOS: 15

<210> SEQ ID NO 1
<211> LENGTH: 24
<212> TYPE: PRT
<213> ORGANISM: Artificial sequence
<220> FEATURE:
<223> OTHER INFORMATION: Synthetic peptide

<400> SEQUENCE: 1

Val Leu Gly Gly Gly Cys Ala Leu Leu Arg Cys Ile Pro Ala Leu Asp
1               5                   10                  15

Ser Leu Thr Pro Ala Asn Glu Asp
            20

<210> SEQ ID NO 2
<211> LENGTH: 24
<212> TYPE: PRT
<213> ORGANISM: Artificial sequence
<220> FEATURE:
<223> OTHER INFORMATION: Synthetic peptide

<400> SEQUENCE: 2

Val Leu Gly Gly Gly Val Ala Leu Leu Arg Val Ile Pro Ala Leu Asp
1               5                   10                  15

Ser Leu Thr Pro Ala Asn Glu Asp
            20

<210> SEQ ID NO 3
<211> LENGTH: 20
<212> TYPE: PRT
<213> ORGANISM: Artificial sequence
<220> FEATURE:
<223> OTHER INFORMATION: Synthetic peptide

<400> SEQUENCE: 3

Lys Phe Gly Ala Asp Ala Arg Ala Leu Met Leu Gln Gly Val Asp Leu
1               5                   10                  15

Leu Ala Asp Ala
            20

<210> SEQ ID NO 4
<211> LENGTH: 20
<212> TYPE: PRT
<213> ORGANISM: Artificial sequence
<220> FEATURE:
<223> OTHER INFORMATION: Synthetic peptide

<400> SEQUENCE: 4

Asn Pro Val Glu Ile Arg Arg Gly Val Met Leu Ala Val Asp Ala Val
1               5                   10                  15

Ile Ala Glu Leu
            20

<210> SEQ ID NO 5
<211> LENGTH: 20
<212> TYPE: PRT
<213> ORGANISM: Artificial sequence
<220> FEATURE:
<223> OTHER INFORMATION: Synthetic peptide

<400> SEQUENCE: 5

Val Ile Ala Glu Leu Lys Lys Gln Ser Lys Pro Val Thr Thr Pro Glu
1               5                   10                  15

```
Glu Ile Ala Gln
            20

<210> SEQ ID NO 6
<211> LENGTH: 20
<212> TYPE: PRT
<213> ORGANISM: Artificial sequence
<220> FEATURE:
<223> OTHER INFORMATION: Synthetic peptide

<400> SEQUENCE: 6

Glu Glu Ile Ala Gln Val Ala Thr Ile Ser Ala Asn Gly Asp Lys Glu
1               5                   10                  15

Ile Gly Asn Ile
            20

<210> SEQ ID NO 7
<211> LENGTH: 20
<212> TYPE: PRT
<213> ORGANISM: Artificial sequence
<220> FEATURE:
<223> OTHER INFORMATION: Synthetic peptide

<400> SEQUENCE: 7

Arg Lys Gly Val Ile Thr Val Lys Asp Gly Lys Thr Leu Asn Asp Glu
1               5                   10                  15

Leu Glu Ile Ile
            20

<210> SEQ ID NO 8
<211> LENGTH: 20
<212> TYPE: PRT
<213> ORGANISM: Artificial sequence
<220> FEATURE:
<223> OTHER INFORMATION: Synthetic peptide

<400> SEQUENCE: 8

Gln Ser Ile Val Pro Ala Leu Glu Ile Ala Asn Ala His Arg Lys Pro
1               5                   10                  15

Leu Val Ile Ile
            20

<210> SEQ ID NO 9
<211> LENGTH: 20
<212> TYPE: PRT
<213> ORGANISM: Artificial sequence
<220> FEATURE:
<223> OTHER INFORMATION: Synthetic peptide

<400> SEQUENCE: 9

Leu Val Leu Asn Arg Leu Lys Val Gly Leu Gln Val Val Ala Val Lys
1               5                   10                  15

Ala Pro Gly Phe
            20

<210> SEQ ID NO 10
<211> LENGTH: 20
<212> TYPE: PRT
<213> ORGANISM: Artificial sequence
<220> FEATURE:
<223> OTHER INFORMATION: Synthetic peptide
```

```
<400> SEQUENCE: 10

Gly Glu Val Ile Val Thr Lys Asp Asp Ala Met Leu Leu Lys Gly Lys
1               5                   10                  15

Gly Asp Lys Ala
            20

<210> SEQ ID NO 11
<211> LENGTH: 20
<212> TYPE: PRT
<213> ORGANISM: Artificial sequence
<220> FEATURE:
<223> OTHER INFORMATION: Synthetic peptide

<400> SEQUENCE: 11

Val Thr Asp Ala Leu Asn Ala Thr Arg Ala Ala Val Glu Glu Gly Ile
1               5                   10                  15

Val Leu Gly Gly
            20

<210> SEQ ID NO 12
<211> LENGTH: 20
<212> TYPE: PRT
<213> ORGANISM: Artificial sequence
<220> FEATURE:
<223> OTHER INFORMATION: Synthetic peptide

<400> SEQUENCE: 12

Ile Val Leu Gly Gly Gly Cys Ala Leu Leu Arg Cys Ile Pro Ala Leu
1               5                   10                  15

Asp Ser Leu Thr
            20

<210> SEQ ID NO 13
<211> LENGTH: 20
<212> TYPE: PRT
<213> ORGANISM: Artificial sequence
<220> FEATURE:
<223> OTHER INFORMATION: Synthetic peptide

<400> SEQUENCE: 13

Glu Ile Ile Lys Arg Thr Leu Lys Ile Pro Ala Met Thr Ile Ala Lys
1               5                   10                  15

Asn Ala Gly Val
            20

<210> SEQ ID NO 14
<211> LENGTH: 20
<212> TYPE: PRT
<213> ORGANISM: Artificial sequence
<220> FEATURE:
<223> OTHER INFORMATION: Synthetic peptide

<400> SEQUENCE: 14

Val Asn Met Val Glu Lys Gly Ile Ile Asp Pro Thr Lys Val Val Arg
1               5                   10                  15

Thr Ala Leu Leu
            20

<210> SEQ ID NO 15
<211> LENGTH: 14
<212> TYPE: PRT
<213> ORGANISM: Artificial sequence
<220> FEATURE:
<223> OTHER INFORMATION: Synthetic peptide
```

```
<400> SEQUENCE: 15

Gly Lys Val Gly Glu Val Ile Val Thr Lys Asp Asp Ala Met
1               5                   10
```